US 7,025,454 B2

(12) United States Patent
Cathey, Jr.

(10) Patent No.: US 7,025,454 B2
(45) Date of Patent: *Apr. 11, 2006

(54) EXTENDED DEPTH OF FIELD OPTICS FOR HUMAN VISION

(75) Inventor: Wade Thomas Cathey, Jr., Boulder, CO (US)

(73) Assignee: The Regants of the University of Colorado, Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/395,577

(22) Filed: Mar. 24, 2003

(65) Prior Publication Data
US 2003/0225455 A1    Dec. 4, 2003

Related U.S. Application Data

(63) Continuation of application No. 09/663,883, filed on Sep. 15, 2000, now Pat. No. 6,536,898.

(51) Int. Cl.
*G02B 7/02* (2006.01)

(52) U.S. Cl. .................. 351/160 R; 351/177; 623/6.17

(58) Field of Classification Search ................ 351/159, 351/41, 160 R, 160 H, 161–162, 177; 359/558–559, 359/563–564; 623/6.11, 6.17; 356/124.5; 382/254–255
See application file for complete search history.

(56) References Cited

U.S. PATENT DOCUMENTS

| 2,959,105 | A | 11/1960 | Sayanagi ........................ 430/4 |
|---|---|---|---|
| 3,054,898 | A | 9/1962 | Westover et al. ........... 250/348 |
| 3,305,294 | A | 2/1967 | Alvarez ...................... 351/169 |
| 3,583,790 | A | 6/1971 | Baker .......................... 359/626 |
| 3,614,310 | A | 10/1971 | Korpel ....................... 348/625 |
| 3,856,400 | A | 12/1974 | Hartmann et al. ............ 356/28 |
| 3,873,958 | A | 3/1975 | Whitehouse ................. 367/126 |
| 4,062,619 | A | 12/1977 | Hoffman ..................... 359/370 |
| 4,082,431 | A | 4/1978 | Ward, III ..................... 359/15 |
| 4,174,885 | A | 11/1979 | Joseph et al. ................. 359/15 |
| 4,178,090 | A | 12/1979 | Marks et al. ............... 396/331 |
| 4,255,014 | A | 3/1981 | Ellis .......................... 359/371 |
| 4,275,454 | A | 6/1981 | Klooster, Jr. ............... 708/821 |
| 4,276,620 | A | 6/1981 | Kahn et al. ................... 369/60 |
| 4,308,521 | A | 12/1981 | Casasent et al. ............ 382/254 |
| 4,349,277 | A | 9/1982 | Mundy et al. .............. 356/604 |
| 4,466,067 | A | 8/1984 | Fontana ..................... 701/300 |

(Continued)

FOREIGN PATENT DOCUMENTS

EP    0531926 B1    3/1993

(Continued)

OTHER PUBLICATIONS

Siebert, J. (Officer), International Search Report received in PCT/US01/26126, international filing date Aug. 20, 2001, Completion Date Jun. 24, 2003, 3 pages.

(Continued)

*Primary Examiner*—Jordan M. Schwartz
(74) *Attorney, Agent, or Firm*—Lathrop & Gage LC (57) ABSTRACT

The present invention provides extended depth of field to human eyes by modifying contact lenses, intraocular implants, and/or the surface of the eye itself. This may be accomplished by applying selected phase variations to these optical elements (e.g., by varying surface thickness of the cornea of the eye). The phase variations EDF-code the wavefront and cause the optical transfer function to remain essentially constant within a range of distances from the in-focus position. This provides a coded image on the retina. The human brain decodes this coded image, resulting in an in-focus image over an increased depth of field.

15 Claims, 5 Drawing Sheets

U.S. PATENT DOCUMENTS

| | | | |
|---|---|---|---|
| 4,480,896 A | 11/1984 | Kubo et al. | 359/707 |
| 4,573,191 A | 2/1986 | Kidode et al. | 382/106 |
| 4,575,193 A | 3/1986 | Greivenkamp, Jr. | 359/495 |
| 4,580,882 A | 4/1986 | Nuchman et al. | 351/161 |
| 4,589,770 A | 5/1986 | Jones et al. | 356/3.64 |
| 4,642,112 A | 2/1987 | Freeman | 623/63 |
| 4,650,292 A | 3/1987 | Baker et al. | 359/720 |
| 4,655,565 A | 4/1987 | Freeman | 351/159 |
| 4,725,881 A | 2/1988 | Buchwald | 348/237 |
| 4,734,702 A | 3/1988 | Kaplan | 342/424 |
| 4,794,550 A | 12/1988 | Greivenkamp, Jr. | 702/160 |
| 4,804,249 A | 2/1989 | Reynolds et al. | 359/721 |
| 4,825,263 A | 4/1989 | Desjardins et al. | 356/603 |
| 4,827,125 A | 5/1989 | Goldstein | 250/234 |
| 4,843,631 A | 6/1989 | Steinpichler et al. | 382/280 |
| 4,936,661 A | 6/1990 | Betensky et al. | 359/692 |
| 4,964,707 A | 10/1990 | Hayashi | 359/371 |
| 4,989,959 A | 2/1991 | Plummer | 359/640 |
| 5,003,166 A | 3/1991 | Girod | 250/201.4 |
| 5,076,687 A | 12/1991 | Adelson | 356/4.04 |
| 5,102,223 A | 4/1992 | Uesugi et al. | 356/607 |
| 5,121,980 A * | 6/1992 | Cohen | 351/161 |
| 5,128,874 A | 7/1992 | Bhanu et al. | 701/301 |
| 5,142,413 A | 8/1992 | Kelly | 359/559 |
| 5,165,063 A | 11/1992 | Strater et al. | 356/4.01 |
| 5,166,818 A | 11/1992 | Chase et al. | 398/201 |
| 5,193,124 A | 3/1993 | Subbarao | 382/255 |
| 5,218,471 A | 6/1993 | Swanson et al. | 359/565 |
| 5,243,351 A | 9/1993 | Rafanelli et al. | 242/351 |
| 5,248,876 A | 9/1993 | Kerstens et al. | 250/559.05 |
| 5,260,727 A * | 11/1993 | Oksman et al. | 351/162 |
| 5,270,825 A | 12/1993 | Takasugi et al. | 348/359 |
| 5,270,861 A | 12/1993 | Estelle | 359/676 |
| 5,270,867 A | 12/1993 | Estelle | 359/692 |
| 5,280,388 A | 1/1994 | Okayama | 359/569 |
| 5,299,275 A | 3/1994 | Jackson et al. | 385/116 |
| 5,301,241 A | 4/1994 | Kirk | 382/166 |
| 5,307,175 A | 4/1994 | Seachman | 358/401 |
| 5,317,394 A | 5/1994 | Hale et al. | 348/207.99 |
| 5,337,181 A | 8/1994 | Kelly | 359/574 |
| 5,426,521 A | 6/1995 | Chen et al. | 359/9 |
| 5,438,366 A | 8/1995 | Jackson et al. | 348/342 |
| 5,442,394 A | 8/1995 | Lee | 348/264 |
| 5,444,574 A | 8/1995 | Ono et al. | 359/708 |
| 5,465,147 A | 11/1995 | Swanson | 356/497 |
| 5,473,473 A | 12/1995 | Estelle et al. | 359/691 |
| 5,476,515 A | 12/1995 | Kelman et al. | 623/6.59 |
| 5,521,695 A | 5/1996 | Cathey, Jr. et al. | 356/4.01 |
| 5,532,742 A | 7/1996 | Kusaka et al. | 348/264 |
| 5,555,129 A | 9/1996 | Konno et al. | 359/569 |
| 5,565,668 A | 10/1996 | Reddersen et al. | 235/462.22 |
| 5,568,197 A | 10/1996 | Hamano | 348/342 |
| 5,572,359 A | 11/1996 | Otaki et al. | 359/386 |
| 5,610,684 A | 3/1997 | Shiraishi | 355/55 |
| 5,640,206 A | 6/1997 | Kinoshita et al. | 348/264 |
| 5,706,139 A | 1/1998 | Kelly | 359/737 |
| 5,748,371 A * | 5/1998 | Cathey et al. | 359/558 |
| 5,751,475 A | 5/1998 | Ishiwata et al. | 359/387 |
| 5,756,981 A | 5/1998 | Roustaei et al. | 235/462.42 |
| 5,965,330 A * | 10/1999 | Evans et al. | 430/321 |
| 5,969,853 A | 10/1999 | Takaoka | 359/370 |
| 5,969,855 A | 10/1999 | Ishiwata et al. | 359/386 |
| 6,021,005 A | 2/2000 | Cathey, Jr. et al. | 359/727 |
| 6,025,873 A | 2/2000 | Nishioka et al. | 348/72 |
| 6,034,814 A | 3/2000 | Otaki | 359/371 |
| 6,037,579 A | 3/2000 | Chan et al. | 250/216 |
| 6,069,738 A | 5/2000 | Cathey, Jr. et al. | |
| 6,091,548 A | 7/2000 | Chen | 359/637 |
| 6,097,856 A | 8/2000 | Hammond, Jr. | 382/312 |
| 6,121,603 A | 9/2000 | Hang et al. | 250/216 |
| 6,128,127 A | 10/2000 | Kusaka | 359/371 |
| 6,144,493 A | 11/2000 | Okuyama et al. | 359/566 |
| 6,172,723 B1 | 1/2001 | Inoue et al. | 349/95 |
| 6,172,799 B1 | 1/2001 | Raj | 359/305 |
| 6,208,451 B1 | 3/2001 | Itoh | 359/247 |
| 6,218,679 B1 | 4/2001 | Takahara et al. | 257/59 |
| 6,219,113 B1 | 4/2001 | Takahara | 349/42 |
| 6,248,988 B1 | 6/2001 | Krantz | 250/201.3 |
| 6,285,345 B1 | 9/2001 | Crossland et al. | 345/87 |
| 6,288,382 B1 | 9/2001 | Ishihara | 250/201.3 |
| 6,337,472 B1 | 1/2002 | Garner et al. | 250/201.3 |
| 6,536,898 B1 * | 3/2003 | Cathey, Jr. | 351/160 R |
| 6,554,424 B1 * | 4/2003 | Miller et al. | 351/160 R |

FOREIGN PATENT DOCUMENTS

| | | |
|---|---|---|
| EP | 0584769 B1 | 3/1994 |
| EP | 0618473 A2 | 10/1994 |
| EP | 0742466 A | 11/1996 |
| EP | 0759573 A2 | 2/1997 |
| EP | 0791846 A2 | 8/1997 |
| EP | 0981245 A2 | 2/2000 |
| GB | 2278750 A | 12/1994 |
| JP | 2000-98301 A | 4/2000 |
| WO | WO 99/57599 | 11/1999 |
| WO | WO-0052516 A | 9/2000 |

OTHER PUBLICATIONS

J. Ojeda-Castaneda, L. R. Berriel-Valdos, and E. Montes, "Spatial filter for increasing the depth of focus", Optics Letters, vol. 10, No. 11, p520-522, Nov. 1985.

W. Chi and N. George, "Electronic imaging using a logarithmic asphere", Optics Letters, vol. 26, No., 12, p 875-877, Jun. 15, 2001.

J. Ojeda-Castaneda, E. Tepichin, and A. Pons, "Apodization of annular apertures: Strehl ratio", Applied Optics, vol. 27, No. 24, p 5140-5145, Dec. 15, 1988.

D. L. Marks, R. A. Stack, D. J. Brady, and J. Van Der Gracht, "Three-dimensional tomography using a cubic-phase plate extended depth-of-field system", Optics Letters, vol. 24, No. 4, p 253-255, Feb. 15, 1999.

S. C. Tucker, W. T. Cathey, and E. R. Dowski, Jr, "Extended depth of field and aberration control for inexpensive digital microscope systems", Optics Express, vol. 4, No. 11, p467-474, May 24, 1999.

J. Ojeda-Castaneda, P. Andres, and A. Diaz, "Annular apodizers for low sensitivity to defocus and to spherical aberration", Optics Letters, vol. 11, No. 8, p 487-489, Aug. 1986.

G. Indebetouw, and H. Bai, "Imaging with Fresnel zone pupil masks: extended depth of field", Applied Optics, vol. 23, No. 23, p 4299-4302, Dec. 1, 1984.

W. T. Welford, "Use of annular apertures to increase focal depth", Journal of the Optical Society of America, vol. 50, No. 8, p 749-753, Aug. 1960.

C. Varamit, and G. Indebetouw, "Imaging properties of defocused partitoned pupils", J. Opt. Soc. Am. A, vol. 2, No. 6, p 799-802, Jun. 1985.

J. Van Der Gracht, E. R. Dowski Jr., M. G. Taylor, and D. M. Deaver, "Broadband behavior of an optical-digital focus-invariant system", Optics Letters, vol. 21, No. 13, p 919-921, Jul. 1, 1996.

G. Hausler, "A method to increase the depth of focus by two step image processing", Optical Communications, vol. 6, No. 1, p 38-42, Sep., 1972.

C. J Cogswell, N. I. Smith, K. G. Larkin, and P. Hariharan, "Quantitative DIC microscopy using a geometric phase shifter", SPIE, vol. 2984, p72-81, 1997.

H. Wang, and F. Gan, "High focal depth with a pure-phase apodizer", Applied Optics, vol. 40, No. 31, p 5658-5662, Nov. 1, 2001.

H. Wang, and F. Gan, "Phase-shifting apodizers for increasing focal depth", Applied Optics, vol. 41, No. 25, p 5263-5266, Sep. 1, 2002.

S. S. Sherif, E. R. Dowski, Jr and W. T. Cathey, "A logarithmic phase filter to extend the depth of field of incoerent hybrid imaging systems", Applied Optics, In press.

D. Kermisch, "Partially coherent image processing by laser scanning", Journal of the Optical Society of America, vol. 65, No. 8, p 887-891, Aug. 1975.

R. J. Pieper and A. Korpel, "Image processing for extended depth of field", Applied Optics, vol. 22, No. 10, p 1449-1453, May 15, 1983.

G. E. Johnson, E. R. Dowski, Jr, and W. T. Cathey, "Passive ranging through wave-front coding: information and application", Applied Optics, vol. 39, No. 11, p 1700-1710, Apr. 10, 2000.

G. Y. Sirat, "Conoscopic holography. I. Basic principles and physical basis", J. Opt. Soc. Am. A, vol. 9, No. 1, p 70-90, Jan. 1992.

E. R. Dowski, Jr, and W. T, Cathey, "Extended depth of field through wave-front coding", Applied Optics, vol. 34, No. 11, p 1859-1866, Apr. 10, 1995.

H. B. Wach, E. R. Dowski,Jr., and W. T. Cathey, "Control of chromatic focal shift through wave-front coding", Applied Optics, vol. 37, No. 23, p 5359-5367, Aug. 10, 1998.

D. Kermisch, "Principle of equivalence between scanning and conventional optical imaging systems", J. Opt. Soc. Am. vol. 67, No. 10, p 1357-1360, Oct. 1977.

J. Ojeda-Castaneda., R. Ramos and A. Noyola-Isgleas, "High focal depth by apodization and digital restoration", Applied Optics, vol. 27, No. 12, p 2583-2586, Jun. 15, 1988.

J.T. McCrickerd, "Coherent processing and depth of focus of annular aperture imagery", Applied Optics, vol. 10, No. 10, p2226-2230, Oct., 1971.

M.Mino and Y. Okano, "Improvement in the OTF of a defocused optical system through the use of shade apertures", Applied Optics, vol. 10, No. 10, p2219-2225, Oct., 1971.

S. Kubo, M. Inui, and Y. Miyake, "Preferred sharpness of photographic color images", Journal of Imaging Science, vol. 29,No. 6, p213-215, Nov./Dec. 1985.

C. J. Cogswell and C. J. R. Sheppard, "Confocal differential interference contrast (DIC) microscopy: including a theoretical analysis of conventional and confocal DIC imaging", Journal of Microscopy, vol. 165, part 1. p 81-101, Jan., 1992.

K. J. Barnard, E. A. Watson and P. F. McManamon, "Nonmechanical microscanning using optical space-fed phased arrays", Optical Engineering, vol. 33, No. 9, p 3063-3071, Sep., 1994.

W. T. Cathey and W. C. Davis, "Imaging system with range to each pixel", J Opt. Soc. Am A, vol. 3, No. 9, p1537-1542, Sep., 1986.

J. E. Greivenkamp, "Color dependent optical prefilter for the suppression of aliasing artifacts", Applied Optics, vol. 29, No. 5, p 676-684, Feb. 10, 1990.

J. T. McCrickerd, "Coherent processing and depth of focus of annular aperture imagery", Applied Optics, vol. 10, No. 10, p 2226-2230, Oct., 1971.

M. Kawakita, K. Iizuka, T. Aida, H. Kikuchi, H. Fujikake, J. Yonai and K. Takizawa, "Axi-version camera: a three-dimension camera", In Three-dimensional Image Capture and Applications III, Brian D. Comer, Joseph H. Nurre, Editors, Proceedings of SPIE, vol. 3958, p 61-70, 2000.

C. Wust and D. W. Capson, "Surface profile measurement using color fringe projection", Machine Vision and Applications, vol. 4, p 193-203, 1991.

Q-S. Chen and M. S. Weinhous, "Sub-pixel shift with fourier transformation to achieve efficient and high quality image interpolation", SPIE, vol. 2, No. 3661, p 728-736, Feb. 1999.

H. Wei, and T. D. Binnie, "High-resolution image reconstruction for multiple low-resolution images", 7th International Conference on Image Processing and Its Applications. Pub. # 465, vol 2 p596-600 (1999).

G. Hausler, and E. Korner, "Imaging with expanded depth of focus", Zeiss Inform, Oberkochen, 29, No. 98E, p 9-13 (1986/1987).

Hecht, Eugene, *Optics*, Second Edition, 1987, pp. 177-181.

Abstract of JP 60247611 A, published Jul. 12, 1985 (Toshiba KK), Patent Abstracts of Japan, May 6, 1986, vol. 010, No. 119 (p-435), 1 page.

Poon, Ting-Chung and Motamedi, Masoud, "Optical/digital incoherent image processing for extended depth of field", Applied Optics vol. 26, No. 21, Nov. 1, 1987, pp. 4612-4615.

Bradburn, Sarah, Cathey, Wade Thomas and Dowski, Edward R., Jr., "Realizations of focus invariance in optical-digital systems with wave-front coding", Applied Optics vol. 36, No. 35, Dec. 10, 1997, pp. 9157-9166.

Van Der Gracht, Joseph, Dowski, Edward R., Jr., Cathey, W. Thomas and Bowen, John P., "Aspheric optical elements for extended depth of field imaging", SPIE vol. 2537, pp. 279-288.

Ojeda-Castaneda, J., and Diaz, A., "High focal depth by quasibifocus", vol. 27, No. 20, p4169-4185, Oct. 15, 1988.

Bartelt, H., Ojeda-Castaneda, J, and Sicre, E, E., "Misfocus tolerance seen by simple inspection of the ambiguity function", Applied Optics, vol. 23, No. 16, p 2693-26696, Aug. 15, 1984.

Ojeda-Castaneda, J., Berriel-Valdos, L. R., and Montes, E., "Ambiguity function as a design tool for high focal depth", Applied Optics, vol. 27, No. 4, p 790-795, Feb. 15, 1988.

Ojeda-Castaneda, J., E. Tepichin, and A. Diaz, "Arbitrarily high focal depth with a quasioplimum real and positive transmittance apodizer", Applied Optics, vol. 28, No. 13, p 2666-2670, Jul. 1, 1989.

Ojeda-Castaneda, J., and L R. Berriel-Valdos, "Arbitrarily high focal depth with finite apartures", Optics Letters, vol. 13, No. 3, p 183-185, Mar., 1988.

Dowski, E, R, Jr., and Cathey, W. T., "Single Ions single-image incoherent passive-ranging systems", Applied Optics, vol. 33, No. 29, p 6762-6773, Oct. 10, 1994.

Cathey, W. T., Frieden, B. R., Rhodes, W. T., and Rushforth, C. K., "Image gathering and processing for enhanced resolution", J. Opt. Soc. Am. A. vol. 1, No. 3, p 241-250, Mar. 1984.

Ojeda-Castaneda, J., and L. R. Berriel-Valdos, "Zono plate for arbitrarlly high focal depth", Applied Optics, vol. 29, No. 7, p 994-997, Mar. 1, 1990.

Schmitt, J. M., Lee, S. L. and Yung, K. M., "An optical coherence microscope with enhanced resolving power in thick tissue", Optics Communications, vol. 142, p 203-207, Oct. 15, 1997.

Shatalin, S. V., Tan, J. B., Juskaitis, R. and Wilson, T., "Polarization contrast imaging of thin films In scanning microscopy", Optics Communications, vol. 118, p 291-299, May 1, 1995.

Fukano, T., "Geometrical cross-sectional imaging by a heterodyne wavelength-scanning Interference confocal microscope", Optics Letters, vol. 25, No. 8, p 548-550, Apr. 15, 2000.

Veldkamp, Wilfrid B., and McHugh, Thomas J., "Binary Optics", Scientific American, May 1, 1992, vol. 286, No. 5, pp. 50-65.

O'Shea, Donald C. and Harrigan, Michael E., "Chapter 33, Aberration Curves in Lense Design", Handbook of Optics, vol. 1, 1996, pp. 33.1-33.5, McGraw-Hill, New York.

* cited by examiner

EXTENDED DEPTH OF FIELD OPTICS FOR HUMAN VISION

CROSS-REFERENCE TO RELATED APPLICATIONS

U.S. Pat. No. 5,748,371 (issued May 5, 1998) entitled "Extended Depth of Field Optical Systems" is incorporated herein by reference. This application is a continuation of commonly-owned and U.S. patent application Ser. No. 09/663,883 (filed Sep. 15, 2000) now U.S. Pat. No. 6,536,898, which is incorporated herein by reference.

BACKGROUND

This invention relates to apparatus and methods for increasing the depth of field and decreasing wavelength sensitivity of incoherent optical systems. In particular, this invention relates to extended depth of focus optics for human vision.

DESCRIPTION OF THE PRIOR ART

In the human eye, it is well known that the accommodation of the lens decreases with age, and that bifocal or trifocal glasses are eventually needed in many cases. When an eye lens must be replaced, an intraocular implant is usually designed for viewing objects at infinity, and the person then uses reading glasses and other glasses of various strengths for vision at closer distances.

Current techniques that are used experimentally in intraocular implants provide two or more foci, for reading and for distance vision, for example. This is done either with a shorter focal length lens placed in the center of a lens of longer focal length, for example, or by use of diffractive optics that provide two foci. The result is one in-focus image and one out-of-focus image. The human brain disregards the out-of-focus image and concentrates on the in-focus image. The major disadvantage of this technique is that if the two images are not aligned (as occurs when the lens is not centered, a frequent occurrence with contact lenses) the images do not line up and the out-of-focus image is apparent. As such a two-foci contact lens moves, the images move with respect to each other. Another disadvantage is loss of contrast. That is, the image looks washed out. The situation is even worse when the object is located between a reading distance and a very long distance; examples include the distance to a computer screen, a television set, or music on a stand. In these cases, two poorly focused images are superimposed.

Another commonly used approach is called monovision: a person is fitted with a lens on one eye for reading, and another lens on the other eye for distance viewing. The brain then selects the best focused image to concentrate on. Images of objects at an intermediate distance cannot be seen clearly. This approach works for many people, but the inability to fuse images that are not both focused has made this solution unusable for many others because the user sees two misregistered images.

The human brain can adapt to unchanging visual conditions, even when they markedly affect the immediate visual perception. For example, the brain is able to adapt to two images, if one is in focus, by concentrating on the in-focus image and ignoring the other.

As another example, the human brain can accommodate for very large distortions present in varifocal lenses, which gradually move from providing clear vision at a distance, for objects seen through the upper portion of the lens, to providing clear vision of close objects when seen through the lower inside part of the lenses. Objects at an intermediate distance can be seen through the center of the lenses.

An extreme example of how the brain can adapt to unchanging conditions was shown in experiments where mirrors were used to invert the images seen by a person. After a day or so, the brain turned the images upside down, so that the person saw a normal image.

The human brain cannot adjust to conventional out-of-focus images, because the amount of blur changes with misfocus, or with distance from the in-focus plane. In addition, the blur is such that some information about the object being seen is lost.

There is a need to extend the depth of focus and, thus, the depth of field, of the human eye by modifying contact lenses, intraocular implants, and/or the surface of the eye itself (with laser surgery, for example).

SUMMARY

An object of the present invention is to provide extended depth of field (EDF) by modifying contact lenses, intraocular implants, and/or natural human eyes. This is accomplished by applying selected phase variations to these optical elements (e.g., by varying surface thickness of the cornea of the eye). These phase variations EDF encode the wavefront and cause the optical transfer function to remain essentially constant within a large range of distances from the in-focus position. The human brain undoes the EDF-coding effects, resulting in an in-focus image over an increased depth of field. While the human brain cannot compensate for general out-of-focus images, where the amount of blur changes with distance from the in-focus plane, it can compensate for the specific EDF-coding misfocus added by the optical mask, because that misfocus does not change with distance, and the phase variations are selected so that little or no information is lost in the process.

For cases where the person still has some refocusing capability, the eye will change focus such that the image of the object being viewed falls into the extended region where the brain can decode the image. In the case of an intraocular implant to replace a damaged lens, the amount of wavefront coding is tailored to give the required amount of invariance in the point spread function. The depth of focus can be increased to be 800% or greater than that of the normal eye.

The selected phase variations to be applied to a particular optical element are typically asymmetric phase distributions that modify the point spread function of the imaging system so that it does not change over a large distance. The optical element may also be circularly symmetric. There are a variety of wavefront coding shapes that can be used, including cubic phase functions.

DETAILED DESCRIPTION OF THE PREFERRED EMBODIMENTS

Figure 1:
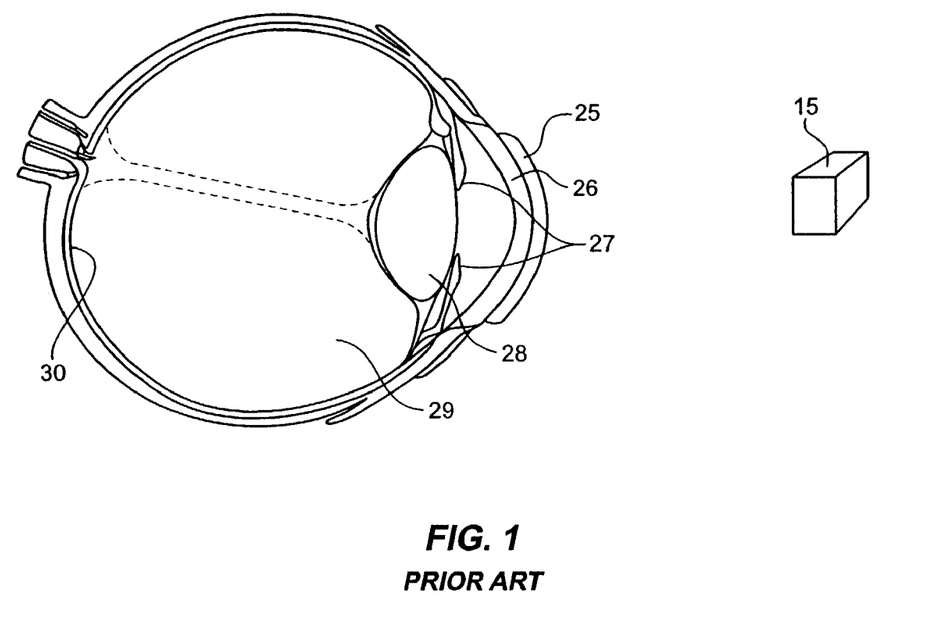
FIG. 1 shows a standard prior art imaging system using a contact lens.

FIG. 1 (prior art) shows a conventional optical imaging system using a contact lens over an eye. Object 15 is imaged through contact lens 25 through the cornea 26, the iris 27, lens 28, and the vitreous humor 29 onto the retina 30. Such a system creates a sharp, in-focus image at the retina 30 only if object 15 is located at or very close to the in-focus object plane. Some accommodation is provided by the lens 28. However, lens 28 hardens with age and loses its ability to refocus. If the distance from the back principal plane of lens 28 to retina 30 is $d_i$, and the focal length of contact lens 25 is f, the distance from the front principal plane of lens 28 to object 15, $d_o$ must be chosen such that:

$$\frac{1}{d_o} + \frac{1}{d_i} - \frac{1}{f} = 0 \quad (\text{Eq. 1})$$

in order for the image at retina 30 to be in adequate focus. The depth of field of an optical system is the distance that the object 15 can move away from the in-focus distance and still have the image be in focus. For a simple system like FIG. 1, the depth of focus is very small, unless the light is bright and the iris is stopped down.

Prior attempts to solve this problem have used contact lenses and optical implants that have multiple (usually two) foci. One focus is correct for objects at infinity, and one is correct for objects at a close distance. This means that two images of an object at one of those locations are formed, one in focus and one out of focus.

Figure 2:
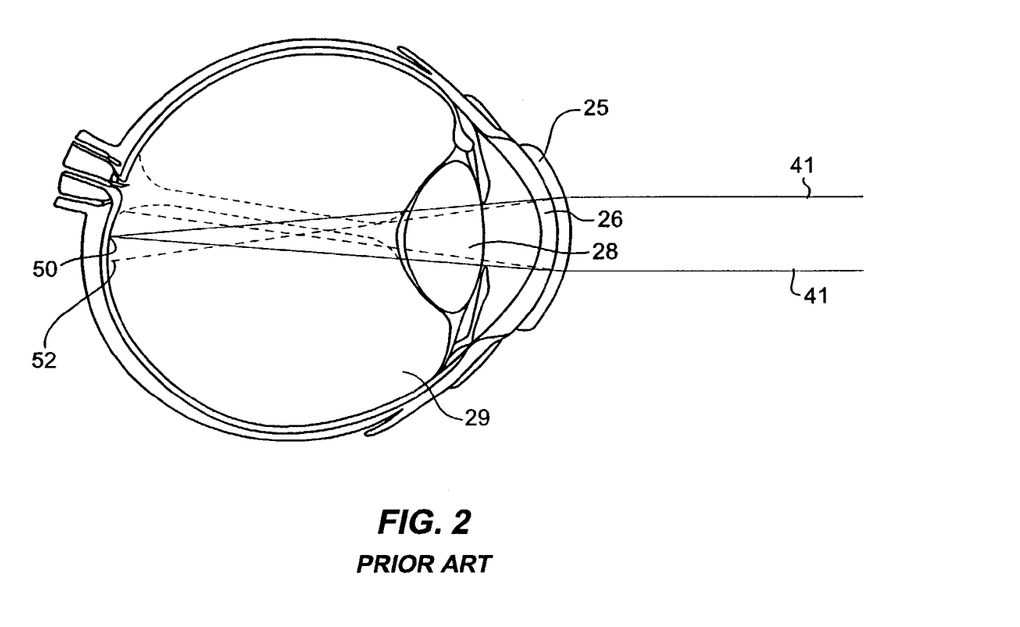
FIG. 2 shows how two images are formed in a standard prior art imaging system

FIG. 2 shows this effect when imaging a point at infinity. Rays 41 form a point image 50 at one of the foci of the combined system formed by contact lens 25, cornea 26, and lens 28. The second focus of the system forms a blurred image 52. When the point object is at a reading distance, the previously blurred image 52 is in focus, and the image 50 becomes blurred. At other distances, neither image is in focus, and the degree of misfocus changes with object location.

A general form of one family of EDF-coding phase variations is:

$$P(x, y) = e^{j(\alpha x^3 + \beta y^3 + \gamma x^2 y + \delta xy^2)}, \; x^2 + y^2 \leq 1. \quad (\text{Eq. 2})$$

Choice of the constants, $\alpha$, $\beta$, $\gamma$ and $\delta$ allow phase functions that are rectangularly separable (with $\gamma = \delta = 0$) to systems whose modulation transfer functions (MTF) are circularly symmetric ($\alpha = \beta = \alpha_0$, $\gamma = \delta = 3\alpha_0$). For simplicity we will use the symmetric rectangularly separable form, which is given by:

$$P(x, y) = e^{j\alpha(x^3 + y^3)}, \; x^2 + y^2 \leq 1, \quad (\text{Eq. 3})$$

where $\alpha$ is a parameter used to adjust the depth of field increase.

Since this form is rectangularly separable, for most analyses its one-dimensional component can be considered:

$$P(x, y) = e^{j\alpha x^3}, \; x^2 \leq 1. \quad (\text{Eq. 4})$$

As the absolute value of $\alpha$ increases, the depth of field increases. The image contrast before post-processing also decreases as $\alpha$ increases. This is because as $\alpha$ increases, the MTF slumps down.

Figure 3:
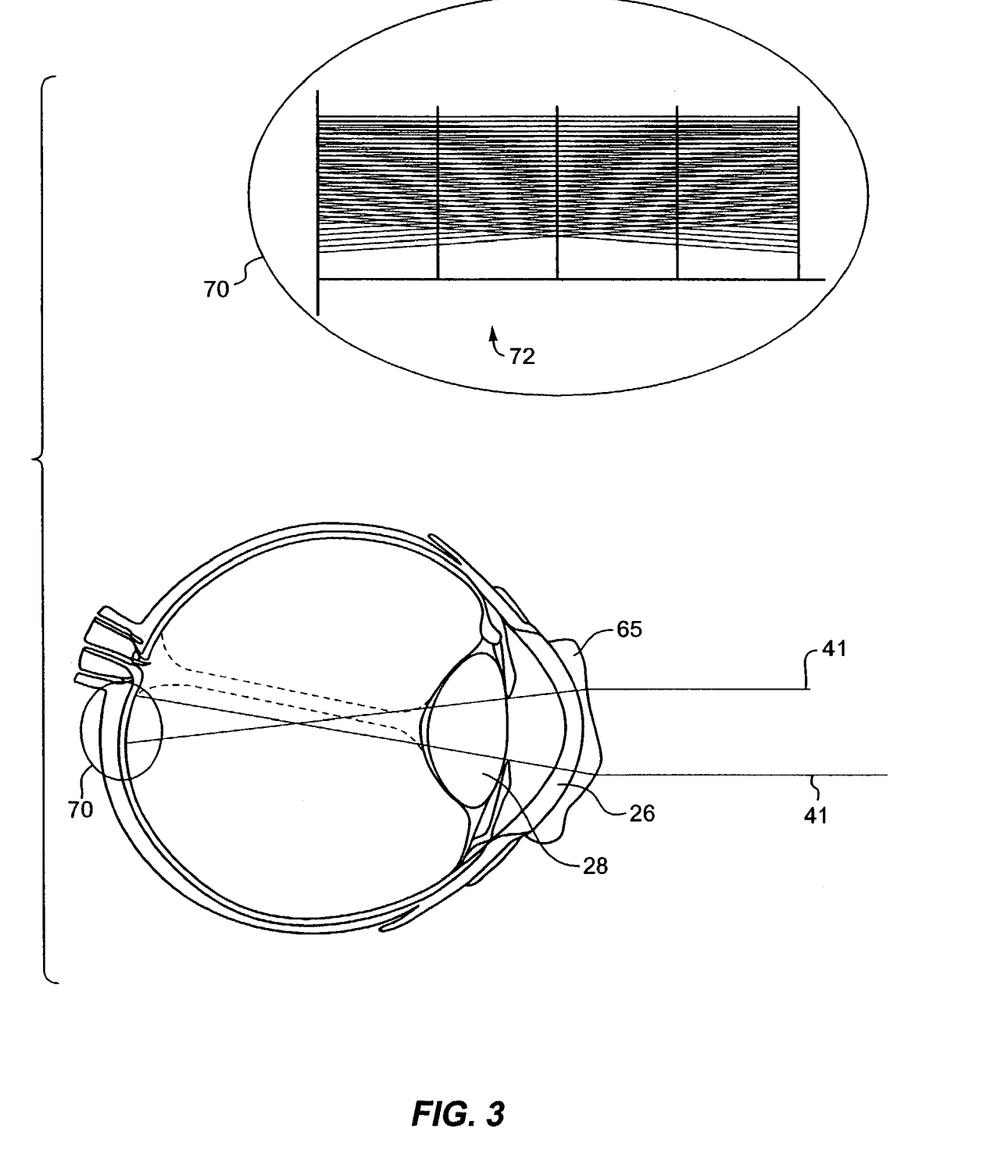
FIG. 3 shows an EDF contact lens imaging system in accordance with one embodiment.

FIG. 3 shows the effect of the EDF-coding phase element on the rays that pass through the eye. Rays 41, which come from a point at infinity and pass through contact lens 65, cornea 26, and lens 28, do not form a useful focus in the eye. Phase coding might be applied by variations in the thickness of lens 65 (exaggerated here for clarity).

An expanded view of the ray pattern near the retina 30 is shown in expanded view 70 where the retina is at plane 72. This is unlike the ray pattern for an eye with a normal contact lens and unlike the ray pattern for an eye with two-foci lens of FIG. 2. As the object point moves in from infinity, the ray pattern in the region of the retina 30, shown expanded in 70, moves to the left, but the cross section of the ray pattern that falls on the retina 30 does not change appreciably. Accordingly, the substantially same ray pattern will fall on the retina without regard to object location. When the object is not a point, the object distribution is convolved with the unchanging ray distribution (e.g., the point spread function). The brain can de-convolve the resulting coded image because the point spread function of the eye, modified with the EDF-coding optics, does not change appreciably. This is in contrast to the changes that normally occur in the point spread function when there is misfocus.

For large enough $\alpha$, the MTF of a system using a cubic phase modulation (PM) mask can be approximated by:

$$|H|(u, \Psi) \approx \sqrt{\frac{\pi}{3|\alpha u|}}, \; u \neq 0, \text{ and} \quad (\text{Eq. 5})$$

$$|H|(u, \Psi) \approx 2, u = 0, \quad (\text{Eq. 6})$$

where u is the spatial frequency in the x direction and $\Psi$ is the degree of misfocus. Thus, the cubic-PM mask is an example of a mask which modifies the optical system to have a near-constant MTF over a range of object distances. The particular range for which the MTF does not substantially vary depends on $\alpha$. This range, and thus the depth of field, increases with $\alpha$. However, the amount that the depth of field can be increased is practically limited by the fact that contrast decreases as $\alpha$ increases. For the human eye, moderate increases in depth of field are typically needed.

Figure 4:
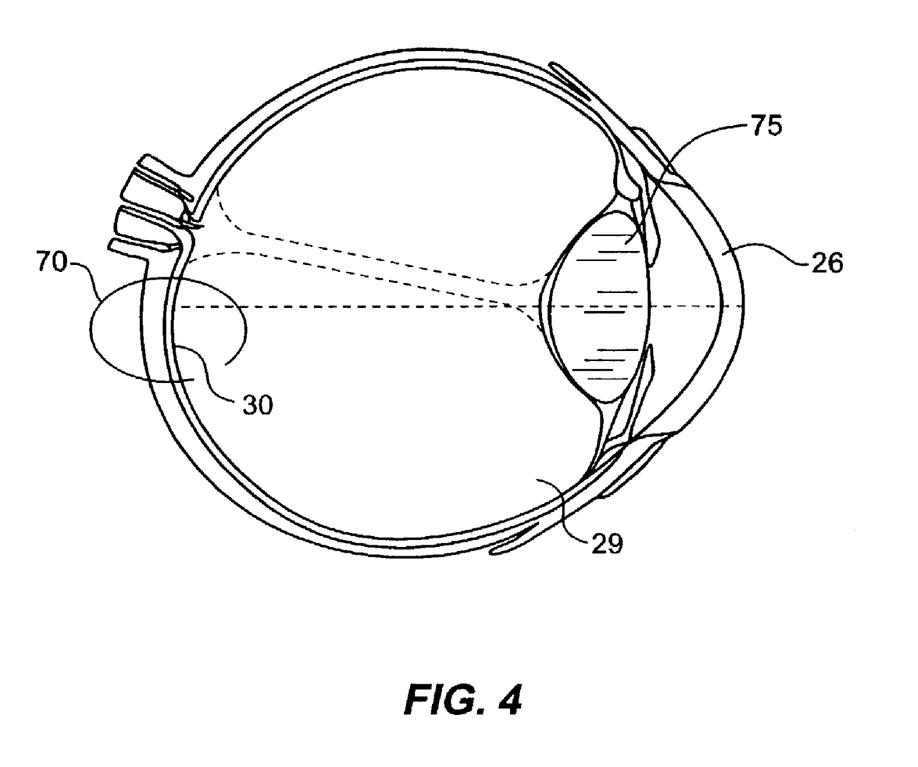
FIG. 4 shows an EDF intraocular implant imaging system in accordance with one embodiment.

FIG. 4 shows an EDF intraocular implant imaging system in accordance with one embodiment where the EDF coding optical shape is on the implant lens 75. The phase coding results in misfocus as shown in expanded view 70 of FIG. 3.

Figure 5:
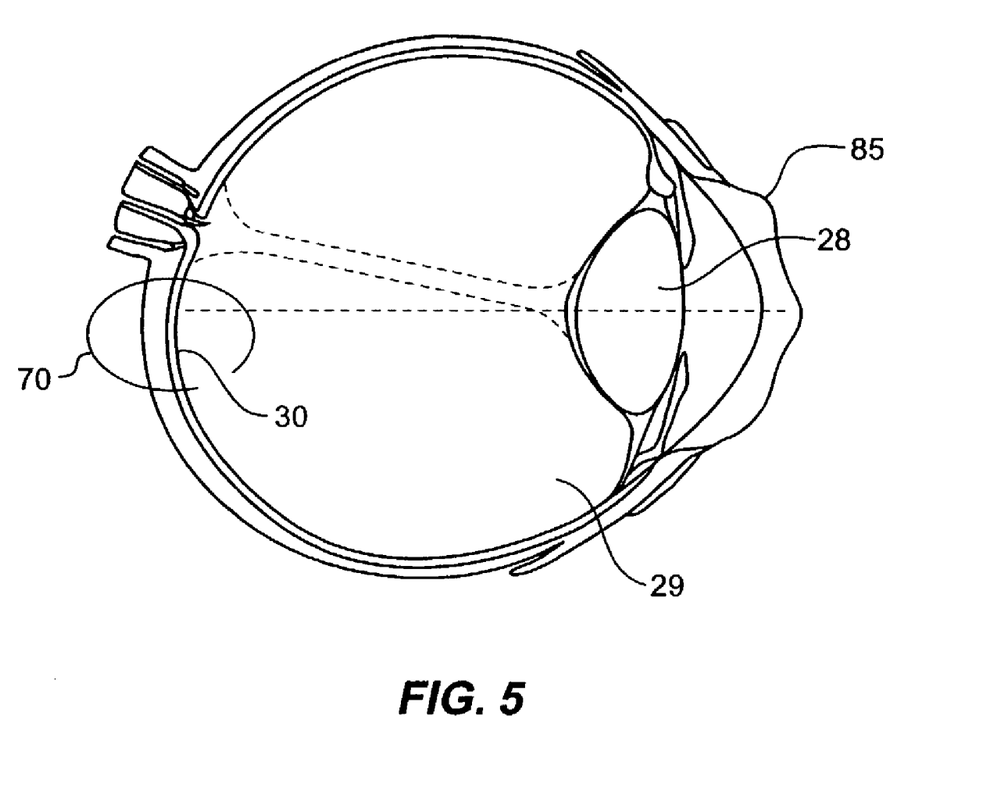
FIG. 5 shows an EDF modified natural eye imaging system in accordance with one embodiment.

FIG. 5 shows an EDF modified natural eye imaging system in accordance with one embodiment where the EDF coding optical shape is on the cornea 85. The cornea 85 can be modified using laser surgery. For example, phase coding is applied through laser-produced variations in the thickness of cornea 85 (thickness of cornea 85 exaggerated here for clarity). The phase coding results in misfocus as shown in expanded view 70 of FIG. 3.

What is claimed is:

1. A system for extending depth of field of an eye, comprising an optical mask positioned between a retina of the eye and an object, the optical mask configured for altering wavefront phase with a continuous phase function, without altering intensity, such that
   an optical transfer function of the eye and the optical mask is less sensitive to distance between the eye and the object as compared to an optical transfer function of the eye without the optical mask.

2. The system of claim 1, the mask comprising thickness variations of one of a cornea of the eye, a contact lens and an intraocular implant.

3. The system of claim 1, the mask configured for implementing a substantially cubic phase function that phase encodes a wavefront of light.

4. The system of claim 1, the mask configured for implementing a circularly symmetric phase function.

5. A method for extending depth of field of an eye, comprising:
   - altering an optical transfer function of the eye thereby providing an altered optical transfer function such that the altered optical transfer function is substantially insensitive to distance between an object and the eye; and
   - encoding phase of light from the object with a continuous phase function that is consistent with the altered optical transfer function.

6. The method of claim 5, wherein said altering includes modifying corneal thickness of the eye so as to alter the optical transfer function of the eye.

7. The method of claim 5, wherein said altering includes placing an optical mask at the eye so as to alter the optical transfer function of the eye.

8. The method of claim 7, wherein said placing the optical mask includes disposing a contact lens on a surface of the eye.

9. The method of claim 7, wherein said placing an optical mask includes implanting an intraocular implant in the eye.

10. The method of claim 5, wherein said encoding includes altering the phase of light with a substantially cubic phase function.

11. The system of claim 3, the mask configured for implementing an asymmetric phase function.

12. The method of claim 7, wherein the optical mask comprises a circularly symmetric phase function.

13. The method of claim 7, wherein the optical mask comprises an asymmetric phase function.

14. A system for extending depth of field of an eye in viewing an object within a range of object distances from the eye, said system comprising:
   - an optical mask disposed between the eye and the object, said optical mask being configured for altering wavefront phase with a continuous phase funtion such that at least one of a modulation transfer function and a point spread function of the combination of the eye and the optical mask is substantially constant over said range.

15. A method for extending depth of field of an eye, said eye including a cornea having a thickness, said method comprising:
   - altering an optical transfer function of the eye thereby providing an altered optical transfer function such that the altered optical transfer function is substantially insensitive over a range of distances between an object and the eye; and
   - encoding phase of light from the object so as to be consistent with the altered optical transfer function,
   - wherein said altering includes modifying the thickness so as to alter the optical transfer function of the eye.

* * * * *